United States Patent
Guo

(10) Patent No.: US 12,186,534 B2
(45) Date of Patent: Jan. 7, 2025

(54) DUAL CARTRIDGE CONTAINER APPLICATOR WITH NEEDLE PENETRATION CONNECTION TO TIP

(71) Applicant: Ethicon, Inc., Somerville, NJ (US)

(72) Inventor: Jianxin Guo, Livingston, NJ (US)

(73) Assignee: Ethicon, Inc., Raritan, NJ (US)

( * ) Notice: Subject to any disclaimer, the term of this patent is extended or adjusted under 35 U.S.C. 154(b) by 428 days.

(21) Appl. No.: 17/127,642

(22) Filed: Dec. 18, 2020

(65) Prior Publication Data

US 2022/0193342 A1 Jun. 23, 2022

(51) Int. Cl.
*A61M 5/19* (2006.01)
*A61M 5/28* (2006.01)
*A61M 5/32* (2006.01)

(52) U.S. Cl.
CPC .............. *A61M 5/19* (2013.01); *A61M 5/286* (2013.01); *A61M 5/3295* (2013.01)

(58) Field of Classification Search
CPC ...... A61M 5/19; A61M 5/286; A61M 5/3295; A61B 17/00491; A61B 2017/00495; B25B 5/12; B25B 5/127; F16L 37/20
See application file for complete search history.

(56) References Cited

U.S. PATENT DOCUMENTS

| | | | |
|---|---|---|---|
| 5,380,780 A | | 1/1995 | Olson |
| 5,569,210 A | * | 10/1996 | Moen ............... A61B 5/150251 |
| | | | 600/576 |
| 6,648,852 B2 | * | 11/2003 | Wirt ....................... A61M 11/06 |
| | | | 604/82 |
| 8,292,619 B2 | | 10/2012 | Peuker et al. |
| 9,149,587 B2 | * | 10/2015 | Kai ......................... A61B 90/30 |
| 9,579,449 B2 | | 2/2017 | Sharma et al. |
| 2003/0055384 A1 | | 3/2003 | Enrenfels et al. |
| 2003/0236552 A1 | | 12/2003 | Roby |
| 2006/0246208 A1 | | 11/2006 | Mansouri et al. |
| 2013/0122314 A1 | | 5/2013 | Ou |

(Continued)

FOREIGN PATENT DOCUMENTS

WO 2012174054 A1 12/2012

OTHER PUBLICATIONS

Office Action for related European Patent Application No. 19849344.7-1109, dated Apr. 8, 2022, 7 pages.

(Continued)

*Primary Examiner* — Nathan R Price
*Assistant Examiner* — Fatimata Sahra Diop

(57) ABSTRACT

A co-reactive liquids delivery applicator, including first and second hollow cylindrical cartridges, each including a stopper at a proximal end and a sealing septum on a distal end and the cartridges containing co-reactive liquids therein, an applicator body including two adjacent chambers configured to secure the first and second cylindrical cartridges, a manifold positioned at a distal portion of the applicator body, the manifold including a pair of hollow needles extending from a proximal portion and a tip connection positioned at a distal portion thereof, and a toggle configured to advance the manifold towards the distal end of the cartridge, wherein upon advancing the manifold each hollow needle penetrates the sealing septum and establishes fluid communication with one of the liquids of the first and second cylindrical cartridges.

12 Claims, 7 Drawing Sheets

(56) References Cited

U.S. PATENT DOCUMENTS

2014/0257234 A1    9/2014   Ma
2014/0357975 A1   12/2014   Nesbitt
2015/0157319 A1    6/2015   Thomas et al.

OTHER PUBLICATIONS

Chen et al., "Rapid kinetics to peak serum antibodies is achieved following influenza vaccination by dry-coated densely packed microprojections to skin", Journal of Controlled Release, vol. 158, No. 1, Oct. 29, 2011, pp. 78-84.
Office Action for related Indian Patent Application No. 202117004766, dated Nov. 23, 2022, 5 pages.
International Search Report for related International Patent Application No. PCT/IB19/56619, dated Dec. 17, 2019, 5 pages.

\* cited by examiner

DUAL CARTRIDGE CONTAINER APPLICATOR WITH NEEDLE PENETRATION CONNECTION TO TIP

FIELD

This invention relates to a co-reactive liquids delivery applicator having a movable manifold for connecting to cartridges containing the liquids.

ENVIRONMENT

In recent years, minimally invasive surgical techniques have emerged as an alternative to conventional surgical techniques to perform a plurality of surgical procedures. Minimally invasive procedures differ from conventional surgical procedures in that a plurality of devices may be introduced into the body through a small incision. As a result, trauma to the body is greatly reduced, thereby decreasing the recovery time of the patient.

One example of a common minimally invasive surgery involves laparoscopic surgical procedures. Laparoscopic procedures may be used to treat hernias, colon dysfunctions, gastroesophageal reflux disease, gallbladder disorders, etc. Typically, the patient undergoing the procedures will return home hours after undergoing surgery.

One challenge presented when performing minimally invasive surgical procedures relates to reducing bleeding at a surgical site when control of bleeding by standard surgical techniques, such as suturing, ligature and cautery, is ineffective or impractical. As opposed to conventional surgical procedures, the surgeon's access to the site of the incision is greatly reduced during minimally invasive procedures and conventional techniques for hemostasis may be difficult to effect.

Recently, the use of tissue sealants and other biological adhesive materials has emerged as an alternate technique for hemostasis. Such tissue sealants may include fibrin, which is comprised of co-reactive thrombin and fibrinogen materials, although other multiple component materials are available. Typically, the individual co-reactive components of the sealant materials are stored in isolated reservoirs. When mixed, these components may coagulate very quickly, yielding a gel within a short period of time, perhaps 10 or 20 seconds. When applied to the exterior of the body, or when considerable access to the application site is possible, the rapid coagulative properties of the tissue sealant are advantageous.

To protect against cross-contamination, multi-barrel co-reactive liquid delivery systems have been developed wherein each reactive material is loaded and sealed in a separate vessel, and then brought together into a unified device, such as a mixing/delivery tip, at the time of use without having to transfer the fluid materials into a separate vial or barrel.

The syringes of such systems can be provided with luer-type connectors at the proximal ends of the syringes, which require a twisting motion to connect and seal with the threads of a conforming device to be attached to the syringe. When side-by-side delivery systems are employed, the twisting motion for locking the luer threads can be awkward.

It would be most convenient to have a co-reactive liquid applicator design which negates the necessity of the twisting motion necessary to connect the syringes to the delivery tips, provides for a low force needle penetration of a cartridge septum and locks up for safety reasons.

SUMMARY

Provided is a co-reactive liquids delivery applicator, comprising first and second hollow cylindrical cartridges, each comprising a stopper at a proximal end of the cartridge and a sealing septum on a distal end of the cartridge and the cartridges containing co-reactive liquids therein, an applicator body comprising two adjacent chambers configured to secure the first and second cylindrical cartridges, a manifold positioned at a distal portion of the applicator body, the manifold comprising a pair of hollow needles extending from a proximal portion of the manifold and not in fluid communication with the first and second hollow cylindrical cartridges, and at least two lumens fluidly connecting the needles to a tip connection positioned at a distal portion thereof, and a toggle configured to advance the manifold towards the proximal end of the applicator, wherein upon advancing the manifold each hollow needle penetrates the sealing septum and establishes fluid communication with one of the liquids of the first and second cylindrical cartridges.

In one form, the toggle includes a toggle latch located on the applicator body, configured to cooperate with a catch on the manifold, such as wherein the toggle latch includes a lever arm pivotally attached to the applicator body and to a draw bar held within the catch on the manifold.

In another form, the sealing septum is held onto the cartridge by a crimped metal cap with an opening at the center.

In yet another form, the applicator body includes two mating halves forming the adjacent chambers for the cylindrical cartridges, and further includes slide guides to direct the needles into contact with septa on distal ends of the cylindrical cartridges.

Advantageously, upon piercing of the cartridge septa the needles conduct the co-reactive liquids from the cartridges into the manifold, and the manifold conducts the co-reactive liquids to the tip connection.

Additionally, the co-reactive liquid delivery applicator can have an elongated delivery tip connected to the tip connection.

Also provided is a co-reactive liquids delivery applicator, comprising an applicator body comprising two adjacent chambers, first and second hollow cylindrical cartridges secured within the adjacent chambers, each of the cylindrical cartridges comprising a stopper at a proximal end of the cartridge and a sealing septum on a distal end of the cartridge, and the cylindrical cartridges containing co-reactive liquids therein, a manifold positioned at a distal portion of the applicator body, the manifold comprising a pair of hollow needles extending from a proximal portion thereof and not in fluid communication with the first and second hollow cylindrical cartridges, and at least two lumens fluidly connecting the needles to a tip connection positioned at a distal portion thereof, and a toggle configured to advance the manifold towards the proximal end of the applicator, wherein upon advancing the manifold each hollow needle penetrates the sealing septum and establishes fluid communication with one of the liquids of the first and second cylindrical cartridges.

In this form, the toggle includes a toggle latch located on the applicator body, configured to cooperate with a catch on the manifold, such as wherein the toggle latch includes a lever arm pivotally attached to the applicator body and to a draw bar held within the catch on the manifold.

In another form, the sealing septum is held onto the cartridge by a crimped metal cap with an opening at the center.

In yet another form, the applicator body includes two mating halves forming the adjacent chambers for the cylindrical cartridges, which can further contain slide guides to direct the needles into contact with septa on distal ends of the cylindrical cartridges.

In this form, upon piercing of the cartridge septa the needles conduct the co-reactive liquids from the cartridges into the manifold, and the manifold conducts the co-reactive liquids to the tip connection.

Also, the co-reactive liquid delivery applicator can have an elongated delivery tip connected to the tip connection.

BRIEF DESCRIPTION OF THE DRAWINGS

The present disclosure is susceptible to various modifications and alternative forms, specific exemplary implementations thereof have been shown in the drawings and are herein described in detail. It should be understood, however, that the description herein of specific exemplary implementations is not intended to limit the disclosure to the particular forms disclosed herein.

This disclosure is to cover all modifications and equivalents as defined by the appended claims. It should also be understood that the drawings are not necessarily to scale, emphasis instead being placed upon clearly illustrating principles of exemplary embodiments of the present invention. Moreover, certain dimensions may be exaggerated to help visually convey such principles. Further where considered appropriate, reference numerals may be repeated among the drawings to indicate corresponding or analogous elements. Moreover, two or more blocks or elements depicted as distinct or separate in the drawings may be combined into a single functional block or element. Similarly, a single block or element illustrated in the drawings may be implemented as multiple steps or by multiple elements in cooperation.

The forms disclosed herein are illustrated by way of example, and not by way of limitation, in the figures of the accompanying drawings and in which like reference numerals refer to similar elements and in which:

Figure 1:
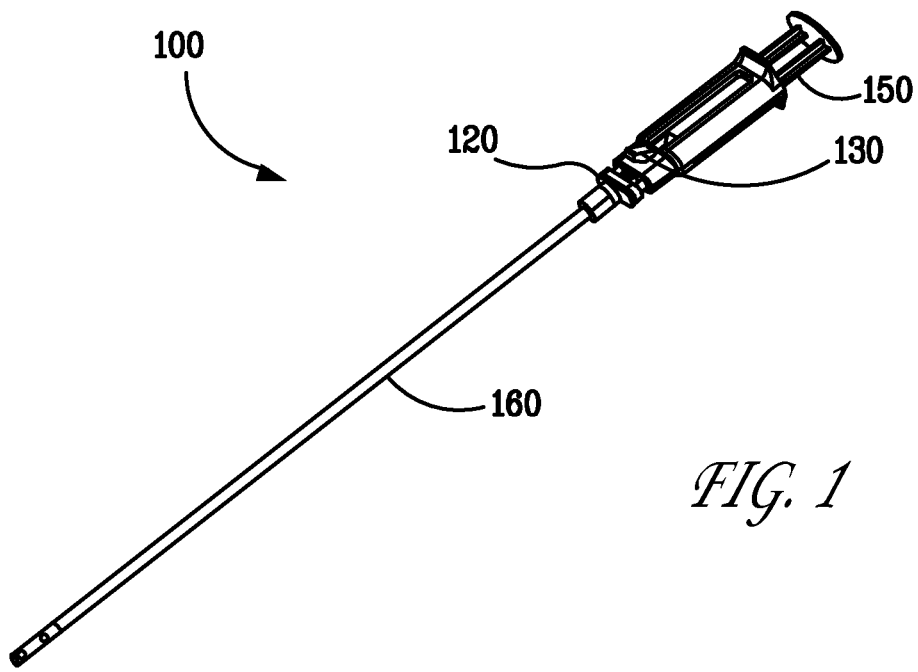
Figure 2:
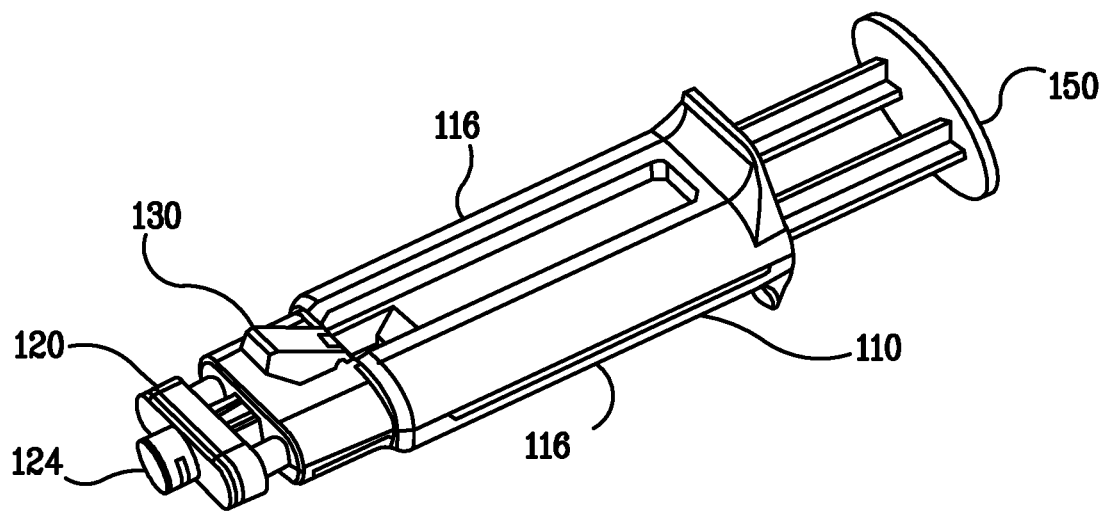
Figure 3:
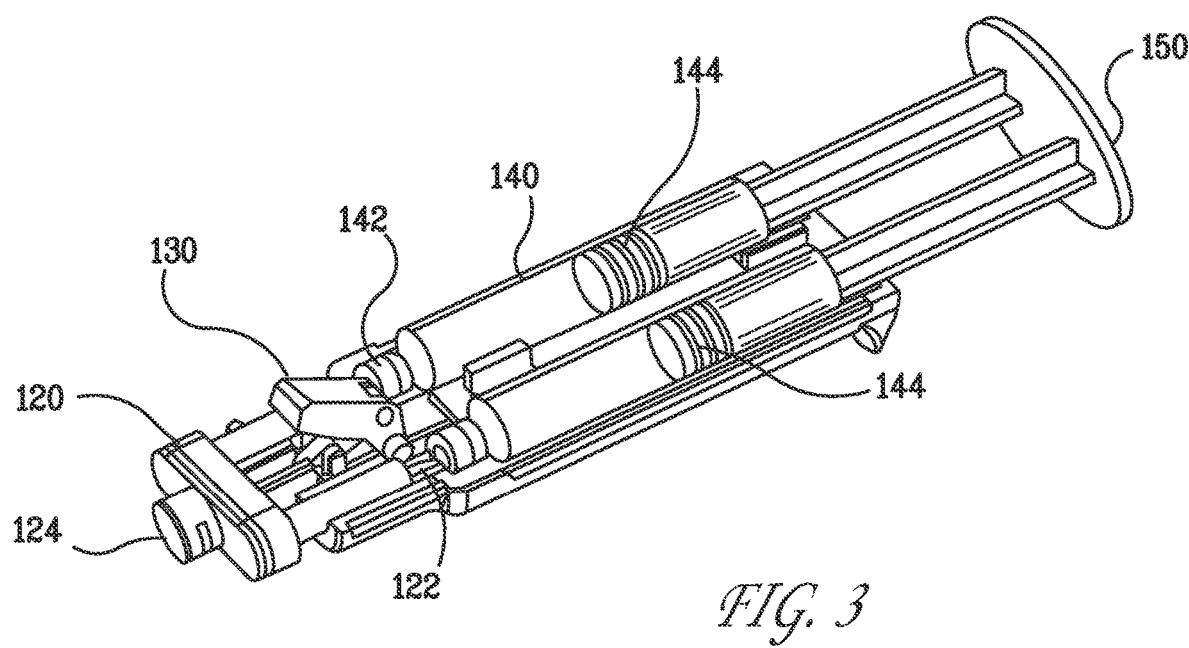
Figure 4:
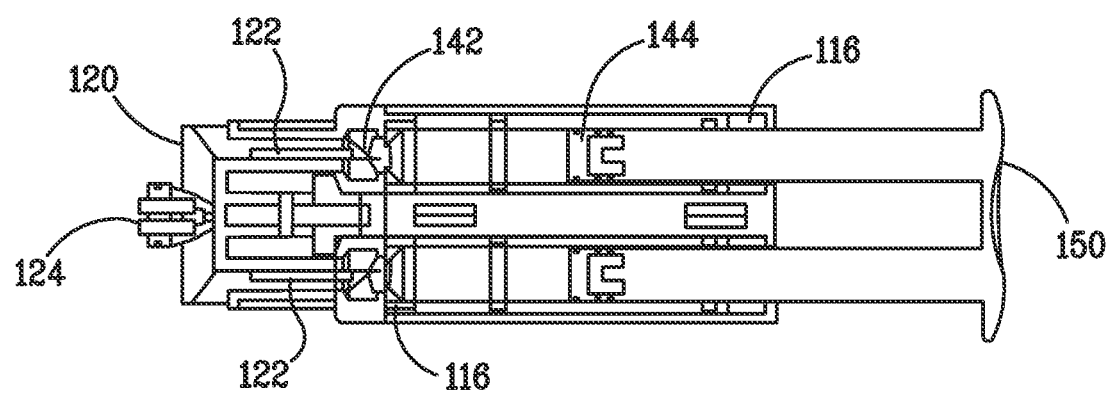
Figure 5A:
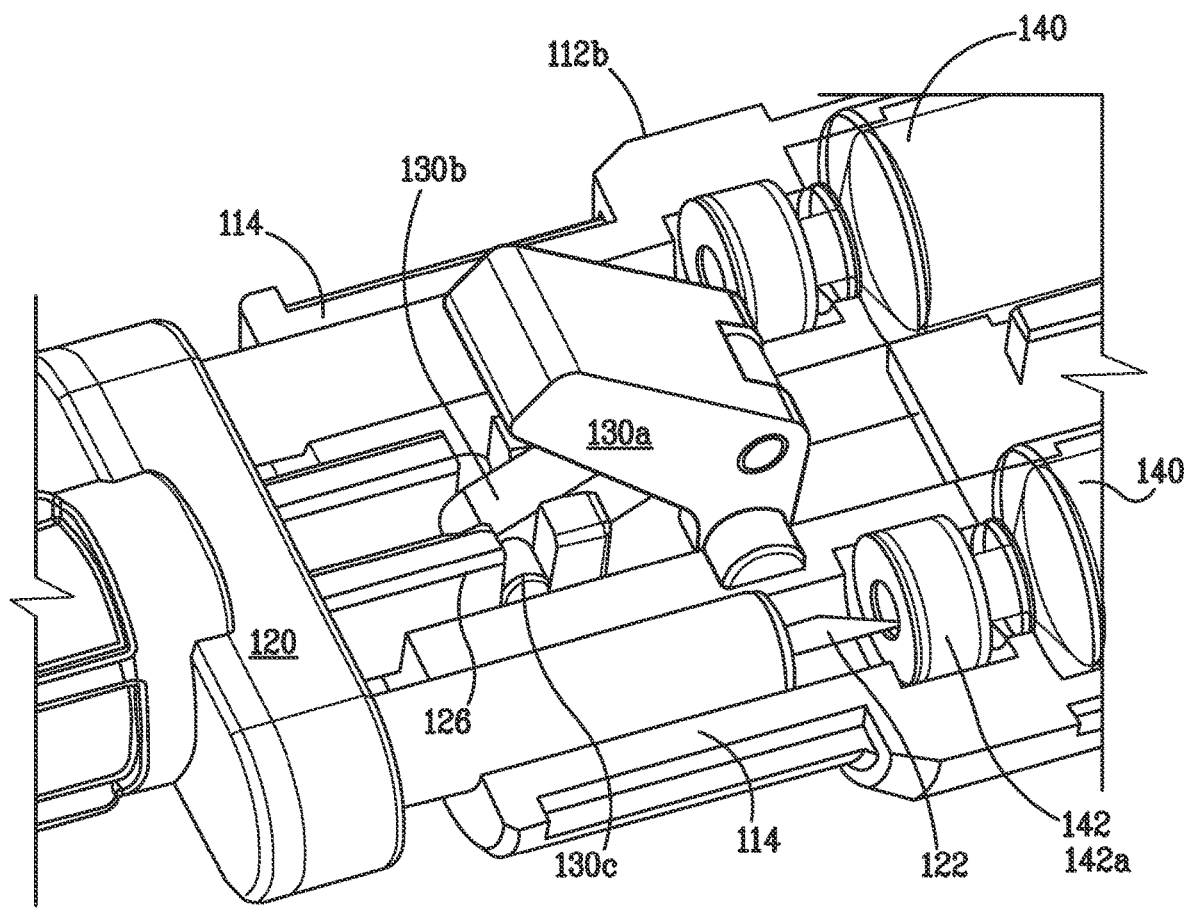
Figure 5B:
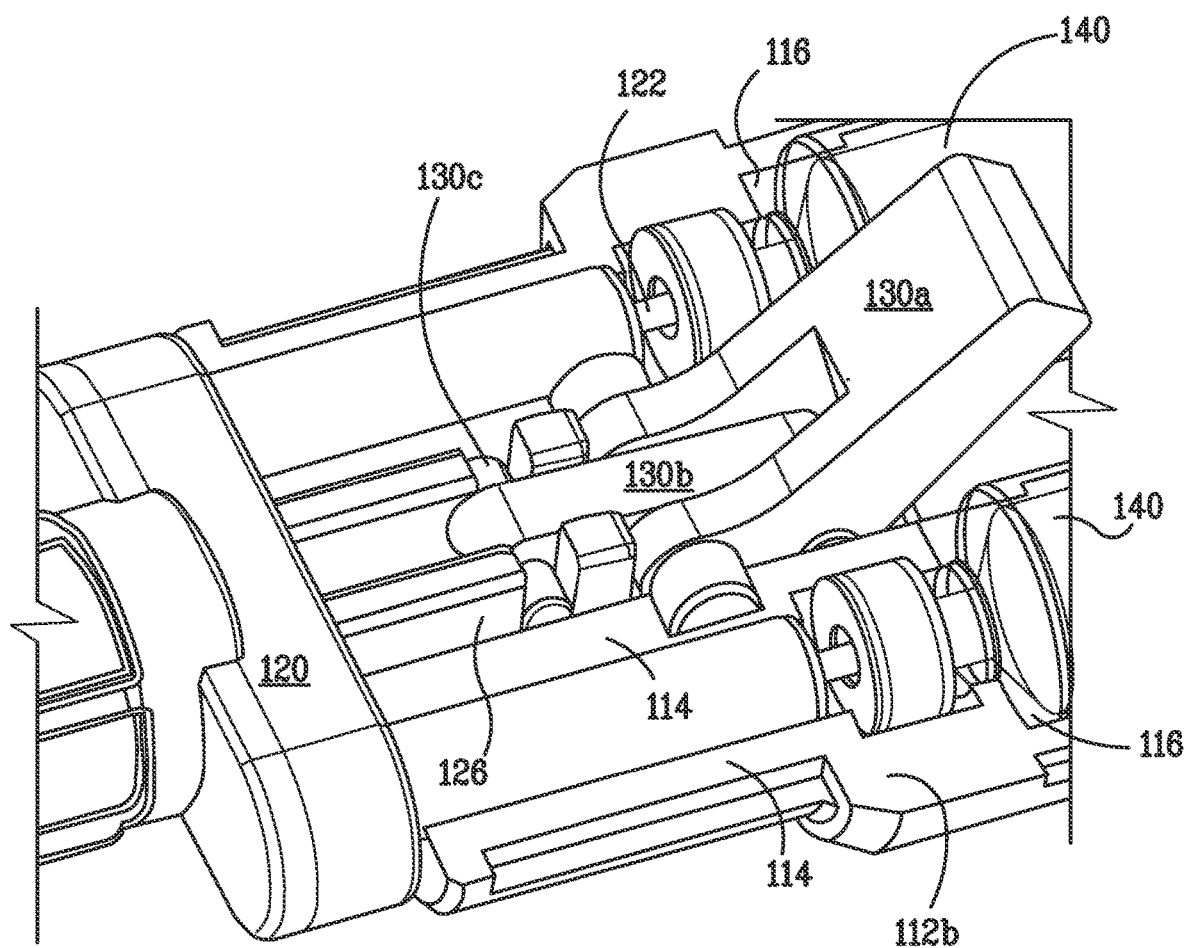
Figure 6:
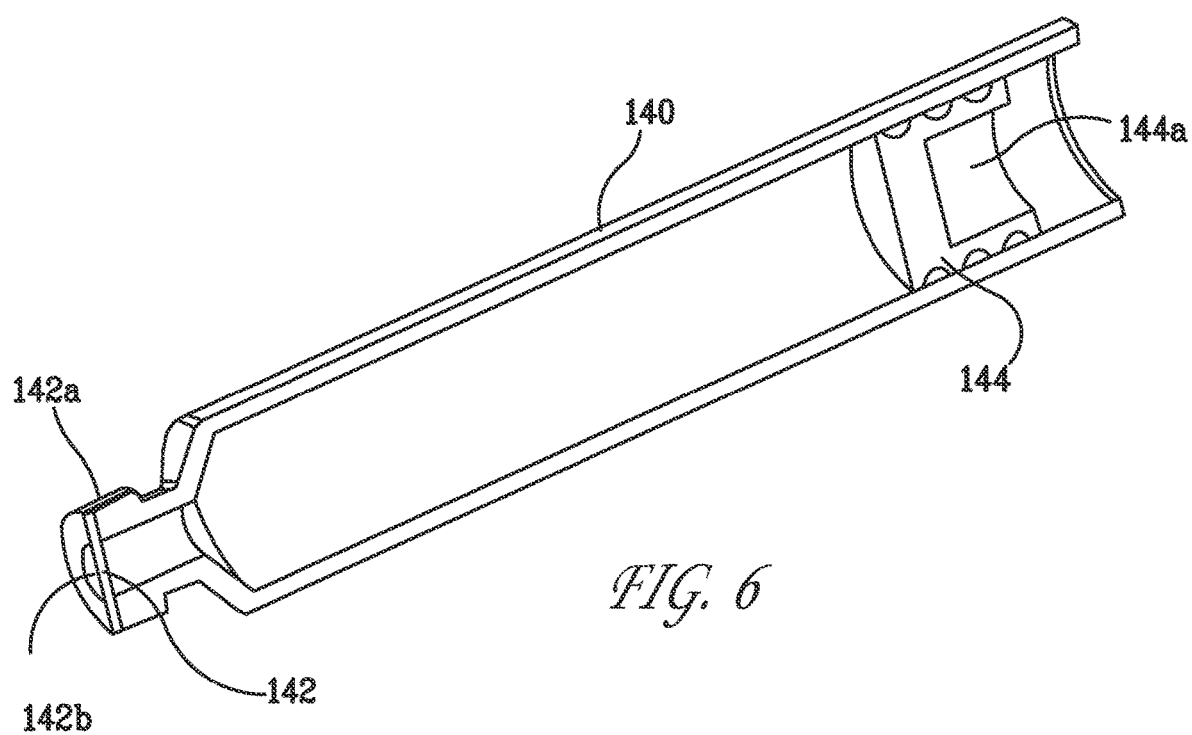
Figure 7:
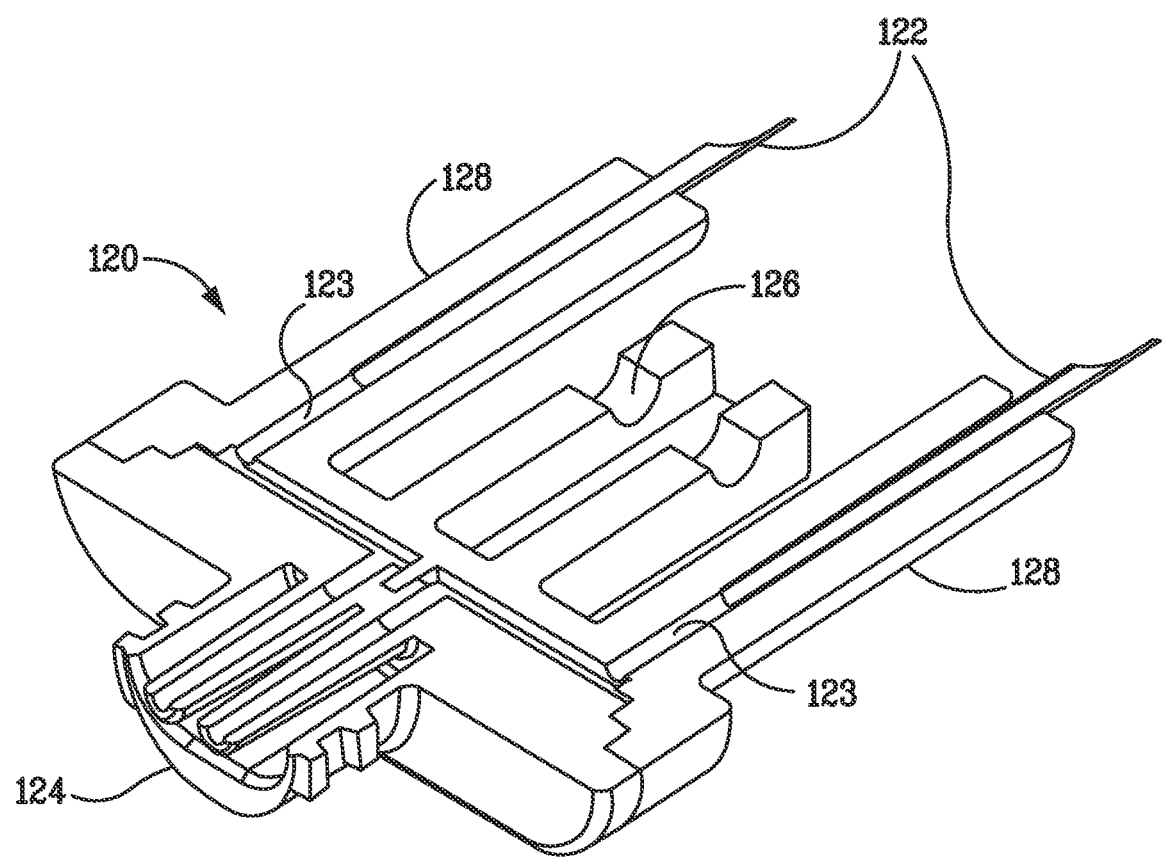

FIG. 1 presents a perspective view of a co-reactive liquid applicator according to the present disclosure;

FIG. 2 presents a close-up, perspective view of the assembled applicator according to the present disclosure;

FIG. 3 presents a partially cutaway view of the assembled applicator of FIG. 2;

FIG. 4 presents a full cutaway view of the applicator of the present disclosure;

FIG. 5A presents a detailed, partially cutaway view of the distal end of the applicator of the present disclosure with the sliding manifold in the unactuated position;

FIG. 5B presents a detailed, partially cutaway view of the distal end of the applicator of the present disclosure with the sliding manifold in the actuated position;

FIG. 6 presents a cutaway view of a cartridge according to the present disclosure; and FIG. 7 presents a cutaway view of the sliding manifold according to the present disclosure.

DETAILED DESCRIPTION

Various aspects will now be described with reference to specific forms selected for purposes of illustration. It will be appreciated that the spirit and scope of the apparatus, system and methods disclosed herein are not limited to the selected forms. Moreover, it is to be noted that the figures provided herein are not drawn to any particular proportion or scale, and that many variations can be made to the illustrated forms.

Each of the following terms written in singular grammatical form: "a," "an," and "the," as used herein, may also refer to, and encompass, a plurality of the stated entity or object, unless otherwise specifically defined or stated herein, or, unless the context clearly dictates otherwise. For example, the phrases "a device," "an assembly," "a mechanism," "a component," and "an element," as used herein, may also refer to, and encompass, a plurality of devices, a plurality of assemblies, a plurality of mechanisms, a plurality of components, and a plurality of elements, respectively.

Each of the following terms: "includes," "including," "has," "having," "comprises," and "comprising," and, their linguistic or grammatical variants, derivatives, and/or conjugates, as used herein, means "including, but not limited to."

Throughout the illustrative description, the examples, and the appended claims, a numerical value of a parameter, feature, object, or dimension, may be stated or described in terms of a numerical range format. It is to be fully understood that the stated numerical range format is provided for illustrating implementation of the forms disclosed herein and is not to be understood or construed as inflexibly limiting the scope of the forms disclosed herein.

Moreover, for stating or describing a numerical range, the phrase "in a range of between about a first numerical value and about a second numerical value," is considered equivalent to, and means the same as, the phrase "in a range of from about a first numerical value to about a second numerical value," and, thus, the two equivalently meaning phrases may be used interchangeably.

It is to be understood that the various forms disclosed herein are not limited in their application to the details of the order or sequence, and number, of steps or procedures, and sub-steps or sub-procedures, of operation or implementation of forms of the method or to the details of type, composition, construction, arrangement, order and number of the system, system sub-units, devices, assemblies, sub-assemblies, mechanisms, structures, components, elements, and configurations, and, peripheral equipment, utilities, accessories, and materials of forms of the system, set forth in the following illustrative description, accompanying drawings, and examples, unless otherwise specifically stated herein. The apparatus, systems and methods disclosed herein can be practiced or implemented according to various other alternative forms and in various other alternative ways.

It is also to be understood that all technical and scientific words, terms, and/or phrases, used herein throughout the present disclosure have either the identical or similar meaning as commonly understood by one of ordinary skill in the art, unless otherwise specifically defined or stated herein. Phraseology, terminology, and, notation, employed herein throughout the present disclosure are for the purpose of description and should not be regarded as limiting.

In the present application the terms "proximal" and "distal" are used to refer to locations relative to the user of the presently disclosed device. For example, a location or position described as "proximal" or "proximal to" or the like is intended to be closer to the hand or body of the user than a location or position described as "distal" or "distal to", or the like, which is intended to be further from the hand or body of the user.

Delivery applicators for co-reactive liquids are well-known. It is necessary to separate the co-reactive liquids during storage and prior to use to avoid undesirable premature reactions between the liquids. Such co-reactive liquids include liquids for forming epoxy resin glues and biological sealants, such as thrombin and fibrinogen, which react when mixed to form fibrin. In use, the delivery applicators deliver the co-reactive liquids separately to the proximity of a site to be treated, and then can be mixed with such as a mixing tip to initiate reaction between them. Presently disclosed is a co-reactive liquid applicator design which provides for low force needle penetration of a reactive liquid cartridge septum and locks up for safety reasons.

FIGS. 1-4 illustrate a co-reactive liquids delivery applicator 100 for distributing at least two co-reactive liquids. The co-reactive liquids can be contained in first and second sealed, hollow cylindrical cartridges 140, each of which has a stopper 144 at a proximal end of the cartridge and a sealing septum 142 on a distal end of the cartridge. The cartridges are secured in an applicator body 110 having two adjacent chambers 116 and the applicator body 110 has a manifold 120, which can be a moveable manifold, such as a sliding manifold, positioned at a distal portion thereof. The manifold 120 has a pair of hollow needles 122 extending from a proximal portion of the manifold and at least two lumens 123 (FIG. 7) fluidly connecting said needles 122 to a tip connection 124 positioned at a distal portion thereof. The applicator body also has a toggle 130 configured to advance the manifold 120 towards the distal end of the cartridge. Upon advancing the manifold 120 proximally toward the applicator body 110 each hollow needle 122 penetrates a sealing septum 142 and establishes fluid communication with one of the co-reactive liquids of the first and second cylindrical cartridges 140. The co-reactive liquid delivery applicator 100 can have an elongated delivery tip 160 connected to the tip connection 124.

FIG. 5A presents a detailed, partially cutaway view of the distal end of the applicator of the present disclosure with the manifold in the unactuated position and FIG. 5B shows FIG. 5A with the manifold in the actuated position. The toggle 130 has a toggle latch 130a located on the applicator body, configured to cooperate with a catch 126 on the manifold 120, such as wherein the toggle latch 130a comprises a lever arm 130b pivotally attached to the applicator body 110 and to a draw bar 130c held within the catch 126 on the manifold 120.

The applicator body 110 comprises two mating halves best seen in FIG. 2, forming adjacent chambers 116 for containing the cylindrical cartridges 140. The bottom chamber of mating halves 116 is indicated by element 112b in FIGS. 5A and 5B. Applicator body 110 also has slide guides 114 to direct the needles 122 held within sliding portions 128 of manifold 120 (FIG. 7) into contact with sealing septa 142 on distal ends of the cylindrical cartridges 140.

FIG. 6 shows a cutaway view of a cartridge container 140 useful with the presently disclosed co-reactive liquid delivery applicator 100. The sealing septum 142 is held onto the cartridge 140 by a crimped metal cap 142a with an opening 142b at the center, through which the septa 142 can be accessed by the manifold needles 122. The proximal end of the cartridge 140 is sealed with a slidable plug or stopper 144, which itself has a hollow proximal end 144a for accepting a distal end of plunger 150 (FIGS. 1-4).

Advantageously, upon piercing of the cartridge septa 142 the needles 122 can conduct the co-reactive liquids from the cartridges 140 into the manifold 120, and the manifold 120 conducts the co-reactive liquids through lumens 123 (FIG. 7) to the tip connection 124.

FIG. 7 presents a cutaway view of the manifold 120 according to the present disclosure. At the distal portion is a tip connector 124, to which a delivery tip 160, such as a mixing tip (not shown), can be connected. The manifold is formed from the hollow needles 122 at the proximal end of the manifold 120, which extend from sliding portions 128, and lumens 123 within the body of the manifold 120, which lead into the tip connection 124. It will be understood that sliding portions 128 are configured to fit into and cooperate with the slide guards 114 formed within a distal portion of the applicator body 110 (FIGS. 5A and 5B). When toggle 130 is actuated by shifting it proximally, the sliding portions 128 of manifold 120 slide within slide guards 114 to force the hollow needles 122 through the central openings 142b of the crimped metal caps 142a and penetrate the sealing septa 142 of the co-reactive liquid cartridges 140. Upon pushing plunger 150, the co-reactive liquids are forced into manifold 120, through tip connector 124 and into delivery tip 160.

EXAMPLES

Further illustrative, non-exclusive examples of systems and methods according to the present disclosure are presented in the following enumerated paragraphs. It is within the scope of the present disclosure that an individual step of a method recited herein, including in the following enumerated paragraphs, may additionally or alternatively be referred to as a "step for" performing the recited action.

PCT1. A co-reactive liquids delivery applicator, comprising:
  first and second hollow cylindrical cartridges, each comprising a stopper at a proximal end of the cartridge and a sealing septum on a distal end of the cartridge and the cartridges containing co-reactive liquids therein;
  an applicator body comprising two adjacent chambers configured to secure said first and second cylindrical cartridges;
  a manifold positioned at a distal portion of the applicator body, the manifold comprising a pair of hollow needles extending from a proximal portion of the manifold and not in fluid communication with said first and second hollow cylindrical cartridges, and at least two lumens connecting said needles to a tip connection positioned at a distal portion thereof; and
  a toggle configured to advance the manifold towards the proximal end of the applicator, wherein upon advancing said manifold each hollow needle penetrates said sealing septum and establishes fluid communication with one of the liquids of the first and second cylindrical cartridges.

PCT2. The co-reactive liquids delivery applicator of paragraph PCT1, wherein the toggle includes a toggle latch located on the applicator body, configured to cooperate with a catch on the manifold.

PCT3. The co-reactive liquids delivery applicator of paragraph PCT2, wherein the toggle latch includes a lever arm pivotally attached to the applicator body and to a draw bar held within the catch on the manifold.

PCT4. The co-reactive liquids delivery applicator of any preceding PCT paragraph, wherein the sealing septum is held onto the cartridge by a crimped metal cap with an opening at the center.

PCT5. The co-reactive liquids delivery applicator of any preceding PCT paragraph, wherein the applicator body includes two mating halves forming the adjacent chambers for the cylindrical cartridges.

PCT6. The co-reactive liquids delivery applicator of any preceding PCT paragraph, wherein the applicator body further includes slide guides to direct the needles into contact with septa on distal ends of the cylindrical cartridges.

PCT7. The co-reactive liquids delivery applicator of any preceding PCT paragraph, wherein upon piercing of the cartridge septa the needles conduct the co-reactive liquids from the cartridges into the manifold, and the manifold conducts the co-reactive liquids to the tip connection.

PCT8. The co-reactive liquids delivery applicator of any preceding PCT paragraph, further including an elongated delivery tip connected to the tip connection.

PCT9. A co-reactive liquids delivery applicator, comprising:
an applicator body comprising two adjacent chambers;
first and second hollow cylindrical cartridges secured within said adjacent chambers, each of the cylindrical cartridges comprising a stopper at a proximal end of the cartridge and a sealing septum on a distal end of the cartridge, and the cylindrical cartridges containing co-reactive liquids therein;
a manifold positioned at a distal portion of the applicator body, the manifold comprising a pair of hollow needles extending from a proximal portion thereof and not in fluid communication with said first and second hollow cylindrical cartridges, and at least two lumens fluidly connecting said needles to a tip connection positioned at a distal portion thereof; and
a toggle configured to advance the manifold towards the proximal end of the applicator, wherein upon advancing said manifold each hollow needle penetrates said sealing septum and establishes fluid communication with one of the liquids of the first and second cylindrical cartridges.

PCT10. The co-reactive liquids delivery applicator of paragraph PCT9, wherein the toggle includes a toggle latch located on the applicator body, configured to cooperate with a catch on the manifold.

PCT11. The co-reactive liquids delivery applicator of paragraph PCT10, wherein the toggle latch includes a lever arm pivotally attached to the applicator body and to a draw bar held within the catch on the manifold.

PCT12. The co-reactive liquids delivery applicator of any of paragraphs PCT9 to PCT11, wherein the sealing septum is held onto the cartridge by a crimped metal cap with an opening at the center.

PCT13. The co-reactive liquids delivery applicator of any of paragraphs PCT9 to PCT12, wherein the applicator body includes two mating halves forming the adjacent chambers for the cylindrical cartridges.

PCT14. The co-reactive liquids delivery applicator of any of paragraphs PCT9 to PCT13, wherein the applicator body further includes slide guides to direct the needles into contact with septa on distal ends of the cylindrical cartridges.

PCT15. The co-reactive liquids delivery applicator of any of paragraphs PCT9 to PCT14, wherein upon piercing of the cartridge septa the needles conduct the co-reactive liquids from the cartridges into the manifold, and the manifold conducts the co-reactive liquids to the tip connection.

PCT16. The co-reactive liquids delivery applicator of any of paragraphs PCT9 to PCT15, further including an elongated delivery tip connected to the tip connection.

INDUSTRIAL APPLICABILITY

The systems and methods disclosed herein are applicable to the medical device industry.

It is believed that the disclosure set forth above encompasses multiple distinct inventions with independent utility. While each of these inventions has been disclosed in its preferred form, the specific embodiments thereof as disclosed and illustrated herein are not to be considered in a limiting sense as numerous variations are possible. The subject matter of the inventions includes all novel and non-obvious combinations and sub-combinations of the various elements, features, functions and/or properties disclosed herein. Similarly, where the claims recite "a" or "a first" element or the equivalent thereof, such claims should be understood to include incorporation of one or more such elements, neither requiring nor excluding two or more such elements.

It is believed that the following claims particularly point out certain combinations and sub-combinations that are directed to one of the disclosed inventions and are novel and non-obvious. Inventions embodied in other combinations and sub-combinations of features, functions, elements and/or properties may be claimed through amendment of the present claims or presentation of new claims in this or a related application. Such amended or new claims, whether they are directed to a different invention or directed to the same invention, whether different, broader, narrower, or equal in scope to the original claims, are also regarded as included within the subject matter of the inventions of the present disclosure.

What is claimed:

1. A co-reactive liquids delivery applicator, comprising: first and second hollow cylindrical cartridges, each comprising a stopper at a proximal end of the cartridge and a sealing septum on a distal end of the cartridge and the cartridges containing co-reactive liquids therein; an applicator body comprising two adjacent chambers configured to secure said first and second cylindrical cartridges; a manifold positioned at a distal portion of the applicator body, the manifold comprising a pair of hollow needles extending from a proximal portion of the manifold and not in fluid communication with said first and second hollow cylindrical cartridges, and at least two lumens fluidly connecting said needles to a tip connection positioned at a distal portion thereof; and a toggle configured to slidably advance the manifold and said pair of hollow needles towards the proximal end of the applicator, wherein upon advancing said manifold, each hollow needle penetrates said sealing septum and establishes fluid communication with one of the liquids of the first and second cylindrical cartridges, wherein the toggle comprises a toggle latch located on the applicator body, wherein the toggle latch comprises a lever arm pivotally attached to the applicator body and to a draw bar held within the catch on the manifold.

2. The co-reactive liquids delivery applicator of claim 1, wherein the sealing septum is held onto the cartridge by a crimped metal cap with an opening at the center.

3. The co-reactive liquids delivery applicator of claim 1, wherein the applicator body comprises two mating halves forming the adjacent chambers for the cylindrical cartridges.

4. The co-reactive liquids delivery applicator of claim 1, wherein the applicator body further comprises slide guides to direct the needles into contact with septa on distal ends of the cylindrical cartridges.

5. The co-reactive liquids delivery applicator of claim 1, wherein upon piercing of the cartridge septa, the needles conduct the co-reactive liquids from the cartridges into the manifold, and the manifold conducts the co-reactive liquids to the tip connection.

6. The co-reactive liquids delivery applicator of claim 1, further comprising an elongated delivery tip connected to the tip connection.

7. A co-reactive liquids delivery applicator, comprising: an applicator body comprising two adjacent chambers; first and second hollow cylindrical cartridges secured within said adjacent chambers, each of the cylindrical cartridges comprising a stopper at a proximal end of the cartridge and a sealing septum on a distal end of the cartridge, and the cylindrical cartridges containing co-reactive liquids therein; a manifold positioned at a distal portion of the applicator body, the manifold comprising a pair of hollow needles extending from a proximal portion thereof and not in fluid communication with said first and second hollow cylindrical cartridges, and at least two lumens fluidly connecting said needles to a tip connection positioned at a distal portion thereof; and a toggle configured to slidably advance the manifold and said pair of hollow needles towards the proximal end of the applicator, wherein upon advancing said manifold, each hollow needle penetrates said sealing septum and establishes fluid communication with one of the liquids of the first and second cylindrical cartridges, wherein the toggle comprises a toggle latch located on the applicator body, wherein the toggle latch comprises a lever arm pivotally attached to the applicator body and to a draw bar held within the catch on the manifold.

8. The co-reactive liquids delivery applicator of claim 7, wherein the sealing septum is held onto the cartridge by a crimped metal cap with an opening at the center.

9. The co-reactive liquids delivery applicator of claim 7, wherein the applicator body comprises two mating halves forming the adjacent chambers for the cylindrical cartridges.

10. The co-reactive liquids delivery applicator of claim 7, wherein the applicator body further comprises slide guides to direct the needles into contact with septa on distal ends of the cylindrical cartridges.

11. The co-reactive liquids delivery applicator of claim 7, wherein upon piercing of the cartridge septa, the needles conduct the co-reactive liquids from the cartridges into the manifold, and the manifold conducts the co-reactive liquids to the tip connection.

12. The co-reactive liquids delivery applicator of claim 7, further comprising an elongated delivery tip connected to the tip connection.

* * * * *